United States Patent
Ding et al.

(10) Patent No.: US 9,988,668 B2
(45) Date of Patent: Jun. 5, 2018

(54) APPARATUS FOR AMPLIFICATION OF NUCLEIC ACIDS

(75) Inventors: Zhimin Ding, Sunnyvale, CA (US); Fang Wu, Sunnyvale, CA (US); Li Liu, Sunnyvale, CA (US)

(73) Assignee: ANITOA SYSTEMS, LLC, Palo Alto, CA (US)

( * ) Notice: Subject to any disclaimer, the term of this patent is extended or adjusted under 35 U.S.C. 154(b) by 395 days.

(21) Appl. No.: 14/128,486

(22) PCT Filed: Jun. 25, 2012

(86) PCT No.: PCT/US2012/044090
§ 371 (c)(1),
(2), (4) Date: Jul. 28, 2014

(87) PCT Pub. No.: WO2012/178210
PCT Pub. Date: Dec. 27, 2012

(65) Prior Publication Data
US 2014/0329244 A1    Nov. 6, 2014

Related U.S. Application Data

(60) Provisional application No. 61/500,523, filed on Jun. 23, 2011.

(51) Int. Cl.
C12M 1/34 (2006.01)
C12Q 1/68 (2018.01)
B01L 7/00 (2006.01)

(52) U.S. Cl.
CPC ............ *C12Q 1/6806* (2013.01); *B01L 7/52* (2013.01); *B01L 2200/028* (2013.01); *B01L 2200/147* (2013.01); *B01L 2200/148* (2013.01); *B01L 2200/16* (2013.01); *B01L 2300/043* (2013.01); *B01L 2300/0654* (2013.01); *B01L 2300/1822* (2013.01); *B01L 2300/1827* (2013.01)

(58) Field of Classification Search
CPC ................. B01L 2300/0627; G01N 21/6452
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,210,015 A | 5/1993 | Gelfand et al. |

(Continued)

OTHER PUBLICATIONS

Patent Cooperation Treaty, International Search Report and Written Opinion, International Patent Application No. PCT/US2012/044090, dated Oct. 16, 2012, 13 Pages.

*Primary Examiner* — William H Beisner
(74) *Attorney, Agent, or Firm* — Morrison & Foerster LLP

(57) ABSTRACT

Described herein is a chip-based apparatus for amplifying nucleic acids, a cartridge housing the apparatus, and methods of using the apparatus for amplification of nucleic acids. More specifically, this invention provides integrated semiconductor chip, manufactured with standard semiconductor manufacturing process, with on-chip circuitry to perform thermal management and optical sensing necessary for amplification of nucleic acids. The apparatus and methods embodied in this invention makes it possible to build a disease diagnosis and prognosis tool that is easy to use, portable and disposable.

36 Claims, 11 Drawing Sheets

(56) References Cited

U.S. PATENT DOCUMENTS

| | | | |
|---|---|---|---|
| 5,866,907 A * | 2/1999 | Drukier | G01N 33/60 |
| | | | 250/328 |
| 6,982,146 B1 | 3/2006 | Schneider et al. | |
| 7,248,359 B2 * | 7/2007 | Boege | G01J 3/10 |
| | | | 356/317 |
| 7,311,794 B2 * | 12/2007 | Joseph | B01L 3/50851 |
| | | | 156/272.2 |
| 7,611,840 B2 | 11/2009 | Xu et al. | |
| 7,705,608 B2 | 4/2010 | Mueller | |
| 7,741,123 B2 | 6/2010 | Pease et al. | |
| 7,803,633 B2 | 9/2010 | Spivey et al. | |
| 2003/0116552 A1 * | 6/2003 | Santoruvo | B01J 19/0093 |
| | | | 219/209 |
| 2005/0079603 A1 * | 4/2005 | Sandstrom | G01N 21/6456 |
| | | | 435/288.7 |
| 2006/0016896 A1 | 1/2006 | Grupp | |
| 2006/0216725 A1 | 9/2006 | Lee et al. | |
| 2006/0246493 A1 | 11/2006 | Jensen et al. | |
| 2006/0292853 A1 | 12/2006 | Dickman | |
| 2007/0184547 A1 | 8/2007 | Handique et al. | |
| 2008/0280350 A1 * | 11/2008 | Moriwaki | B01L 7/52 |
| | | | 435/286.1 |
| 2009/0097527 A1 | 4/2009 | Hosking et al. | |
| 2009/0130745 A1 * | 5/2009 | Williams | B01L 3/5027 |
| | | | 435/287.2 |
| 2009/0148910 A1 | 6/2009 | Korampally et al. | |
| 2009/0180516 A1 | 7/2009 | Den Toonder et al. | |
| 2009/0247418 A1 | 10/2009 | Castro | |
| 2010/0285573 A1 | 11/2010 | Leck et al. | |
| 2010/0297640 A1 | 11/2010 | Kumar et al. | |
| 2010/0303690 A1 | 12/2010 | Howell et al. | |
| 2012/0088691 A1 * | 4/2012 | Chen | B01L 7/52 |
| | | | 506/12 |

* cited by examiner

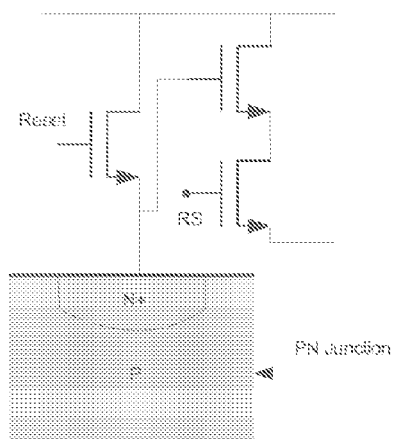
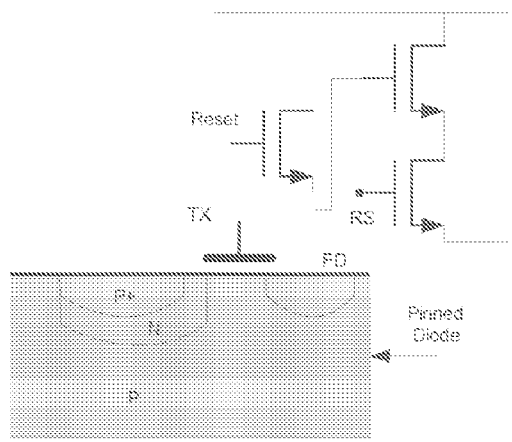
FIG. 7A          FIG. 7B
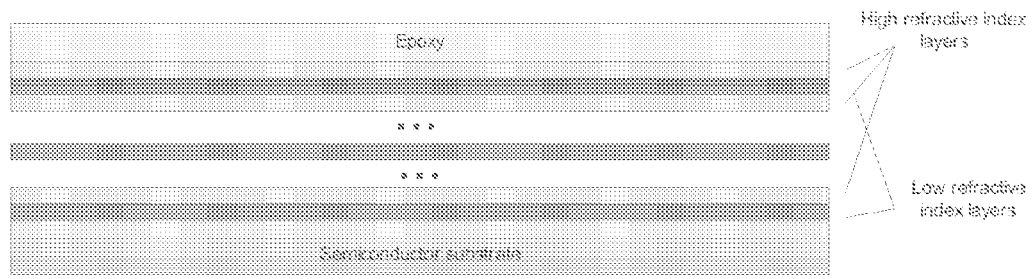
FIG. 8

APPARATUS FOR AMPLIFICATION OF NUCLEIC ACIDS

CROSS-REFERENCE TO RELATED APPLICATIONS

This application is a U.S. national phase application under 35 U.S.C. § 371 of International Application No. PCT/US2012/044090, filed on Jun. 25, 2012, which claims the priority benefit of U.S. Provisional Application No. 61/500,523, filed on Jun. 23, 2011.

BACKGROUND OF THE INVENTION

Described herein is a chip-based apparatus for amplifying nucleic acids, a cartridge housing the apparatus, and methods of using the apparatus for amplification of nucleic acids. More specifically, this invention provides integrated circuit semiconductor chip, manufactured with standard semiconductor manufacturing process, to perform thermal management and optical sensing necessary for on-chip amplification and detection of nucleic acids. The apparatus and methods embodied in this invention make it possible to build a disease diagnosis and prognosis tool that is easy to use, portable and disposable.

The detection and quantification of nucleic acid is becoming more and more important in: (1) medicine, specifically disease diagnosis or prognosis and drug discovery; (2) crop and animal breeding and authentication; (3) forensic identification; 4) environmental monitoring and industrial processing. The Polymerase Chain Reaction, or PCR, is a method for replicating a nucleic acid of interest many times. PCR is widely used in detecting small amounts of nucleic acids in a sample. It is particularly useful for the detection of diseases, including infectious diseases and cancer.

Real time PCR, also known as qPCR, allows the accumulation of PCR-amplified nucleic acids to be monitored in real time instead of at the end point of the reaction. Real time monitoring of the buildup of PCR products allows one to better manage the reaction and quantify the concentration of the target nucleic acid.

Conventional instruments for real time PCR are typically bulky and costly. Examples are BioRad iCycler®, Life Technologies StepOne® real time PCR system, Roche Diagnostics LightCycler® 2.0, Qiagen's Roto-Gene® system. The reasons are twofold. The conventional thermal management method depends on a structure with large thermal capacity to achieve precise control of temperature. Typically this is achieved through the use a sizable metal heating block and a cooling reservoirs which regulate the temperature of the samples contained in plastic tubes.

Moreover, to achieve real time monitoring of PCR product accumulation, optical systems are involved to detect optically labeled target molecules. In a conventional design, optical monitoring is achieved through use of many discrete components, such as photo multipliers (PMT, a type of vacuum tube), discrete photodiodes or CCD sensors. Optical excitation is achieved through the use of lamps, laser diodes or high power LEDs. These components and the associated lenses, filters and mechanical structures typically require substantial space and diminish the portability of the associated apparatus.

PCR devices are typically designed to house multiple "wells", where samples contained in tubes are placed. This design is necessary to perform PCR on many different samples, some of which are negative or positive controls. To perform optical detection of many samples with optical detection systems made of discrete components typically requires a motion control system to move sample tubes individually into the optical detection pathway. Again, this typical design increases the complexity, size and cost of the PCR device. It also introduces an additional artifact: detection times are different for different samples. This artifact reduces sample-to-sample reproducibility.

Efforts have been made to allow PCR to occur on a "chip", with very small reaction volumes (e.g., WAFERGEN's SmartChip™ and BECKMAN COULTER's AmpliGrid™ system). However, like many biological lab-on-chip systems, these "chips" are nothing more than a passive substrate made of plastic and/or glass. These "chips" alone cannot perform the necessary functions for PCR. In order for PCR reactions to occur, these "chips" need to be placed into a bulky thermal cycler much like the conventional ones described above. Many of these "chip"-based thermal cyclers in the market are in fact bigger and more expensive than the mainstream tube based thermal cyclers. At the end of the reaction, the results of typical "chip"-based PCR systems are generally detected or monitored with the assistance of a bulky and expensive optical system such as a fluorescent microscope.

Each year, a large population of the world is affected by outbreaks of various types of infectious diseases, such as SRS, influenza/H1N1/H5N1, foot-and-mouth disease, TB, HBV, HCV, HIV, etc. Many of these diseases, at least at the onset, are treatable. However, the lack of health care in many poorer regions of the world coupled with a dense population causes many instances of disease to go undiagnosed, untreated or mistreated. Untreated or mistreated pathogens spread, mutate and evolve into pandemics, affecting the lives of millions and billions of dollars. A need therefore exists for effective diagnostic tools that are easy to use, low cost, portable and disposable, such that the diagnostic procedures can be reliably performed at the point-of-care.

SUMMARY OF THE INVENTION

Embodiments of the present invention provide an apparatus and a corresponding method for amplification of a nucleic acid in a sample. In one embodiment, the apparatus comprises a semiconductor substrate including one or more components formed on the substrate. In a related embodiment, a temperature sensor is formed on the substrate, where the temperature sensor is configured to detect the sample's temperature and send the temperature information to a processor configured to provide heating and cooling instructions. In a related embodiment, a heating element is provided wherein the heating element is configured to heat the sample responsive to instructions provided by the processor. In yet another related embodiment, the substrate comprises a light sensor configured to measure light emission from the sample. In yet another related embodiment, the substrate comprises a biocompatible coating for receiving the sample.

In one aspect, a semiconductor substrate is provided upon which various circuitry components are formed monolithically. In one aspect, these components include those that are necessary for performing real time PCR, e.g., temperature sensors, heaters, and light sensors. In another aspect, the semiconductor substrate with components formed on top is coated with a thin film layer that is at least bio-compatible and preferably hydrophilic for receiving the bio-chemical sample that contains the PCR reagent mixed with fluid containing target DNA strands to be amplified.

In one embodiment, a microprocessor is also formed on the semiconductor substrate. The processor fetches instructions from memory (e.g., memory formed on the semiconductor substrate) and executes programs to automate the real time PCR process. In another embodiment, memory devices are formed on the semiconductor substrate. The memory devices contain instructions and data for use by the processor to automate and perform functions related to amplifying nucleic acid, using the real time PCR protocol. Preferably, a portion of the memory is non-volatile, and stores information about the parameters of the reaction and/or chemical reagents that are used in the reaction.

In one embodiment, the components and circuits formed on the semiconductor chip are designed and manufactured in accordance to the standard monolithic semiconductor manufacturing process, such as the complementary-metal-oxide-semiconductor, or CMOS process.

Exemplary embodiments also include various other circuit components including timers, analog to digital converters (ADC), communication controllers, voltage regulators, and IO pads.

In all embodiments, the semiconductor chip rests on a solid support object for structural integrity. An example of such a support is the printed circuit board (PCB), on which metal conductive traces are formed. The semiconductor chip makes electric contact with the conductive traces on the solid support through bonding wires.

In another aspect of these embodiments, a bio-compatible and hydrophilic coating on the semiconductor substrate is provided. In related embodiments, an epoxy polymer is used. Additional layers of thin-film coating can be applied to the semiconductor chip surface, such that the coating layer can act as a wavelength filter. In one variation of this implementation, the coatings are made of zinc sulfide and Cryolite compounds.

Alternatively, a light wavelength filter can be made of coated glass, quartz or transparent polymer (e.g., polycarbonate or polypropylene) and laminate on top of the semiconductor substrate. In a related embodiment, a wavelength filter is "patterned" such that different portions of the filter have different wavelength filtering characteristics. In this aspect, different light sensors are subject to different filtering effects and the pixels can preferably sense light of different wavelengths. This is useful for detecting the activity of different molecular probes with different peak emission wavelengths.

In certain aspects, the reagent sample that is received by the coated semiconductor chip has the volume of 0.1 µL to 200 µL.

In one embodiment, the heating element is made of a transistor component formed on the semiconductor substrate. An example of such a transistor is a power MOSFET device common in integrated circuit semiconductor chips.

In another embodiment, the heating element is made of resistors formed on the semiconductor substrate. An example of such a resistor is a poly silicon resistor, common in integrated circuitry semiconductor chips.

In yet another aspect of the embodiments, the light sensor is made of an array of active pixel circuitry. Each of these pixels consists of a photodiode device and a read out circuitry made of 3 or 4 transistors. Furthermore, additional analog and digital circuitries are included to allow for suppression of noise generated by the pixels, e.g., by comparing output from different pixels. In another embodiment of this technique, noise suppression is achieved by comparing pixel read outs at different time periods, while keeping other operating conditions (e.g., temperature) constant.

In a preferred embodiment, among the circuits formed on the substrate are one or more analog to digital converters (ADC). These converters convert analog information produced by the sensors to digital information for efficient communication and further processing by the processor.

In yet another aspect of the embodiments, a communication controller is included on the chip. The communication controller helps to communicate information obtained or processed on the chip to the outside of the chip. Specifically, it can package information sent from the sensors, embedded CPU, or memory and transmit such information serially and, preferably, in digital form. Conversely, it can receive information from outside the chip and send the information to the on-chip control circuitry, embedded CPU or memory. The communication controller can transmit or receive functions through the IO pads of the chip.

When the communication controller communicate the information gathered from the chip to the outside of the chip in digital form and serially, error checking methods such as parity check or cyclic redundancy check (CRC) are typically utilized, in conjunction with a resend mechanism to enhance communication reliability.

In additional embodiment, the invention provides an external instrument device for interfacing with a human operator. The external instrument device consists of user interface features such as a keypad and display. Furthermore, the external instrument device may provide power and a clock to the semiconductor chip apparatus.

A human operator operates the external instrument device through its user interface features, namely keypad and display. The operator can initiate, terminate, and monitor the progress of the reaction. The operator can also modify the instructions and data stored in memory which the processor uses to perform reaction control.

In another embodiment, the external instrument device also provides assisted cooling and optical excitation to the semiconductor chip-based PCR apparatus mentioned above.

In a preferred embodiment an excitation light source is included in the external instrument device. In one embodiment, the excitation light source consists of one or more light emitting diodes (LEDs) and associated excitation filters.

In a variation of the invention, the processor resides outside the chip, thus is part of the instrument. The processor controls the on-chip components such as heaters, temperature sensors, and light sensor by communicating with them through the communication interface.

In one embodiment, the external instrument device provides assisted cooling function to the semiconductor chip. In one aspect of the embodiment, the external instrument achieves assisted cooling of the semiconductor chip using a fan. The fan receives command from the processor that controls the PCR process.

In another aspect of the embodiment, the external instrument achieves assisted cooling of the semiconductor chip using a solid state cooling device such as the Peltier device. The Peltier receives command from the processor that controls the PCR process, regardless of whether the processor itself is embedded on the chip or not. In another embodiment, the external instrument device is connected to the Internet, either through wired interface, such as USB or Ethernet, or wirelessly, such as through Wi-Fi or through a mobile network, e.g., a GSM network, a 3G network, etc.

The present invention also provides a cartridge apparatus comprising the semiconductor chip mentioned above, where the semiconductor chip is housed in a chamber within the cartridge. The semiconductor chip will form at least one surface of the chamber. The surface formed by the semiconductor chip can be vertical, horizontal or tilted relative to the direction of gravity.

In yet another embodiment, more than one chamber can be formed in the cartridge. Each of these chambers has at least one surface spanned by the semiconductor chip. Each of these chambers can receive samples for PCR reactions. Preferably, these chambers are segregated to isolate the fluid contained in these chambers.

Included in the invention are openings for the chamber to receive samples. Each chamber has one or more openings, e.g., one opening to receive the samples and an additional opening to provide a vent to avoid formation of bubbles.

In one embodiment, certain portions of the biochemical reagents are pre-stored in the chambers of the cartridge prior to delivery of the cartridge to the user site. A preferred method of pre-store biochemical reagents is to store such reagents in freeze-dried or "lyophilized" form.

In another embodiment, at least one wall of a chamber of the apparatus is optically transmissive, allowing excitation light to pass through this wall and into the reagent mixture, whereby fluorescent labeled bio-chemical compounds are excited.

In a preferred embodiment, the direction of excitation light is chosen such that the excitation light does not incident on the sensor surface directly. Preferably, the direction of the excitation light should be perpendicular to the normal of the light sensor surface, i.e. the semiconductor chip.

As mentioned earlier, the processor receives information from the temperature sensor and sends instructions to the heaters to control the temperature. The processor accomplishes this task by establishing a desired temperature called temperature set point, then calculating the difference between the measured temperature and the temperature set point. The processor then combines a proportional, integral and differential aspect of the difference to generate instructions to the heating element.

Analog and digital circuitry may be included to suppress the inherent noises generated by the light sensors. Because noise may be correlated to the temperature of the chip, this circuitry can further use the information from the temperature sensor to estimate noise and improve noise suppression.

Among the various instructions and data stored in memory and executed by the processor, there exists a set of instructions and data and/or programs to perform self calibration in factory. Specifically, the self calibration program temperature provided by the temperature sensor to the actual temperature the chip is exposed to in the factory, which is known. The program then calculates a set of correction factors to account for any inaccuracies of the temperature sensor. These correction factors are specific for each instance of the device and stored in the memory of the device. These factors are then applied during the normal operation of the device.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 6 shows an exemplary implementation of a transistor-based heater, comprising a single Power MOSFET. The heater can be turned on by applying logic input (shown as a 5V logic signal) to the base. A resistor is applied between the source and ground. The resistor value and Vgs determines the power dissipation on the transistor when it is turned on.

FIG. 7 shows a schematic representation of pixel circuitry, comprising a photo diode and a read out circuitry consists of 3 (in FIG. '7a') or 4 (in FIG. '7b') transistors. The photodiode can be a reverse-biased PN junction photodiode (in FIG. '7a') or a P+NP pinned diode (in FIG. '7b').

FIG. 8 illustrates a wavelength filter coating consisting of alternating layers of two or more dielectric materials of different refractive indices, such as zinc sulfide (refractive index of 2.35) and cryolite (refractive index of 1.35).

DETAILED DESCRIPTION OF THE INVENTION

Definitions

Figure 1:
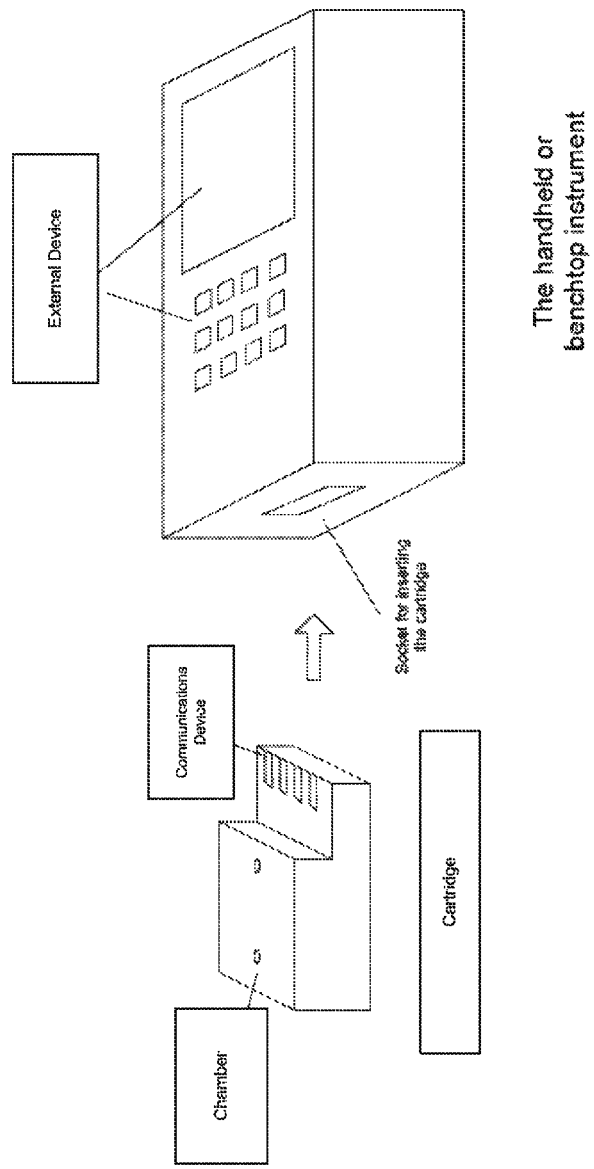
FIG. 1 shows the cartridge and external device. The cartridge houses one more chambers within. For each chamber, there is an opening for loading sample and optionally another one for venting purposes. The external device is a handheld or bench top instrument. It has essential user interface features such as a display and a keypad. The external instrument device also has an opening for the cartridge to plug into. The cartridge makes electric contacts with the external instrument device through an array of electric contacts.
Figure 2:
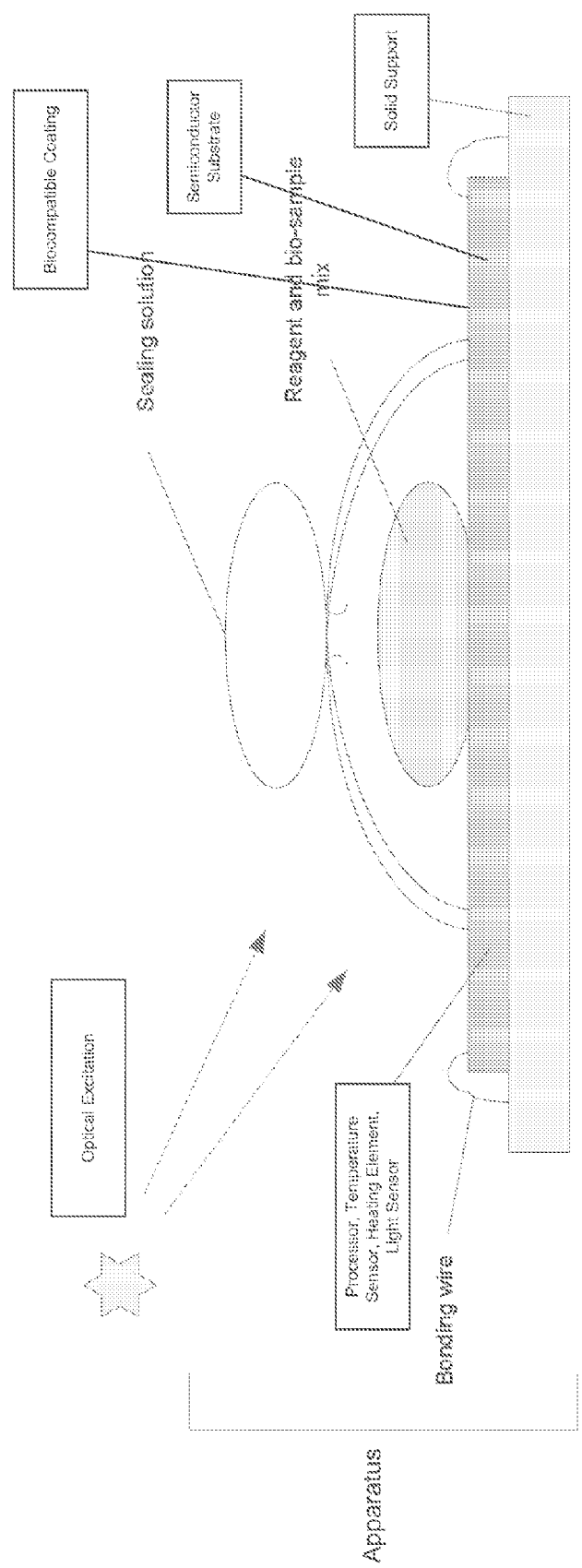
FIG. 2 shows an embodiment of the apparatus for amplifying nucleic acids. Specifically shown here is the semiconductor substrate on top of which many circuitry components are formed. The semiconductor chip rests on a solid support. A chamber is formed over the semiconductor substrate. A mix of bio-sample and PCR reagent is housed inside the chamber. The semiconductor chip is coated with a layer of thin film coating to provide a bio-compatible interface with the sample fluid and act as a wavelength filter for the image sensor formed on the semiconductor substrate. There are one or more openings for loading samples into the chamber. The openings can be sealed during the reaction. Part of the chamber wall can be transparent to receive optic excitation from a light source outside the chamber.
Figure 3:
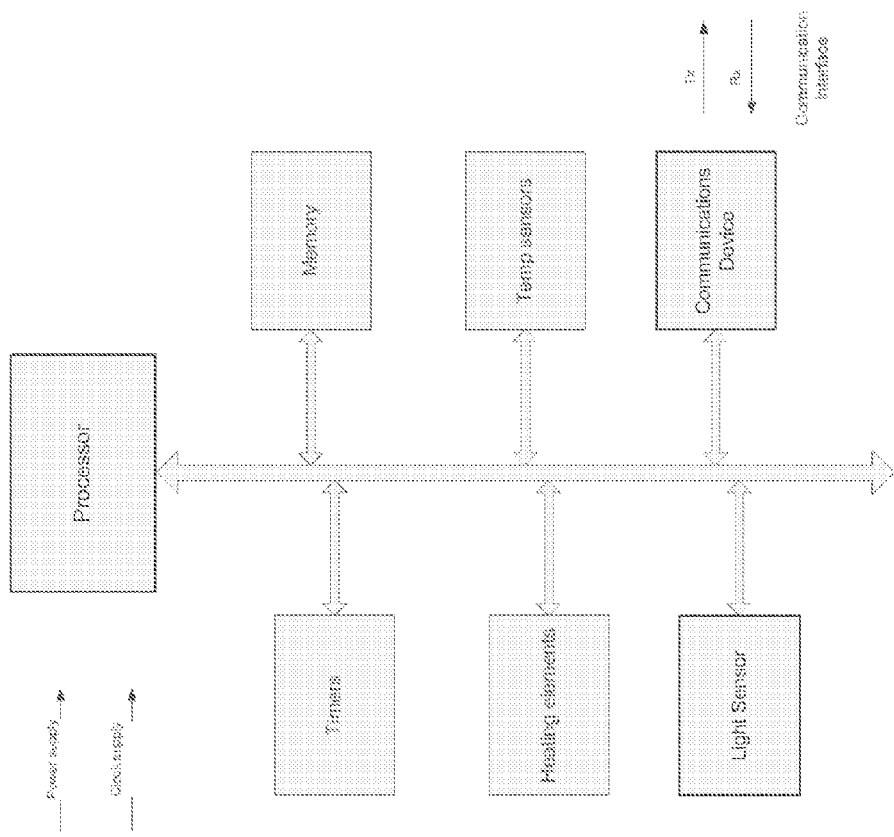
FIG. 3 shows a functional diagram of the circuitry formed on the semiconductor substrate. The functional blocks of the chip—temperature sensor, heater, light sensor, communication controller, and memory are shown here. A processor is connected to all these functional blocks through a set of electric connections known as the bus. The circuitry receives power and clock supply from outside the chip. It can also communicate with the outside through electric connections shown as TX and RX lines, with the help of the communication controller.
Figure 4:
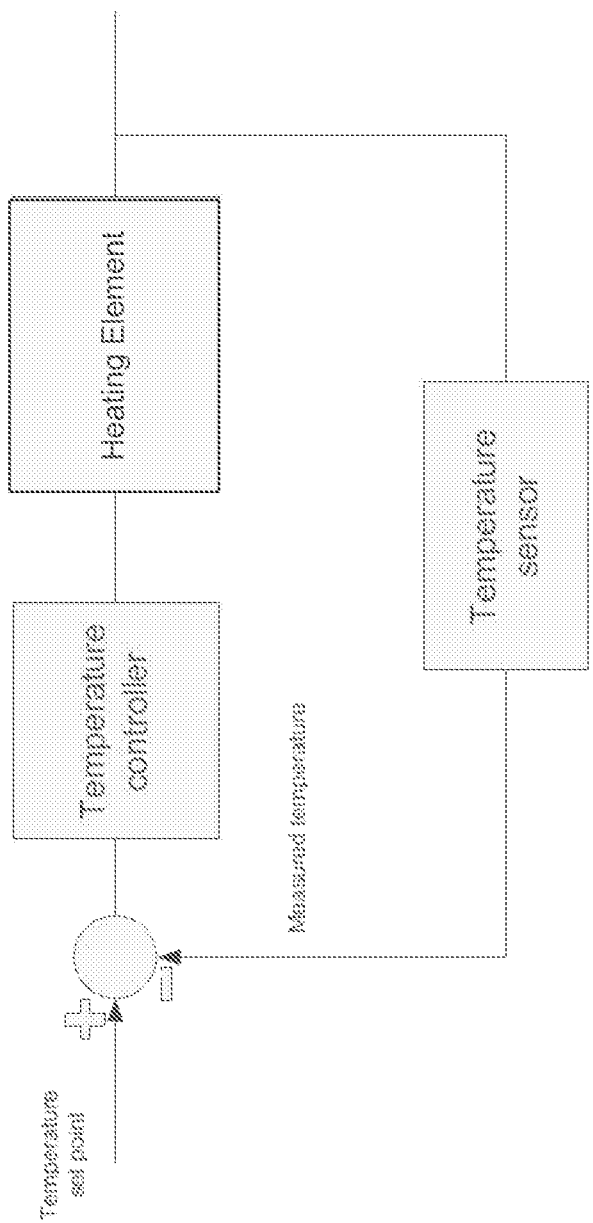
FIG. 4 shows a block diagram illustrating the architecture and algorithm for temperature control using feedback. A desired temperature level is given as the temperature set point. The actual temperature is measured by the temperature sensor. The difference between the two is used by the temperature controller to calculate and generate instructions to the heating element, which acts as the actuator of the control system.

Terms used in the claims and specification are defined as set forth below unless otherwise specified.

The term "nucleic acids" refers to biological molecules that include DNA (deoxyribonucleic acid) and RNA (ribonucleic acid), which are essential for life. Together with proteins, nucleic acids make up the most important macromolecules; each is found in abundance in all living things.

The term "semiconductor" refers to a material with electrical conductivity due to electron flow (as opposed to ionic conductivity) intermediate in magnitude between that of a conductor and an insulator. Semiconductor materials are the foundation of modern electronics, including radio, computers, telephones, and many other devices.

The term "microprocessor" refers to a device that incorporates the functions of a computer's central processing unit (CPU) on a single integrated circuit (IC, or microchip). It is a multipurpose, programmable, clock-driven, and register-based electronic device that accepts binary data as input, processes it according to instructions stored in its memory, and provides results as output.

The term "complementary metal-oxide-semiconductor" or "CMOS" refers to a technology for constructing integrated circuits. CMOS technology is used in microprocessors, microcontrollers, static RAM, and other digital logic circuits. CMOS technology is also used for analog circuits such as image sensors, data converters, and highly integrated transceivers for many types of communication.

The term "hydrophilic" refers to properties of a molecule or portion of a molecule that is typically charge-polarized and capable of hydrogen bonding, having an affinity for water.

The term "reagents" refers to compounds or mixtures, usually composed of inorganic or small organic molecules that are used to affect a transformation on an organic substrate.

The term "transistor" refers to a semiconductor device used to amplify and switch electronic signals.

The term "Peltier effect" is the effect of creating a heat flux between the junction of two different types of materials. A Peltier cooler, heater, or thermoelectric heat pump is a solid-state active heat pump which transfers heat from one side of the device to the other side against the temperature gradient (from cold to hot), with consumption of electrical energy.

Reference in the specification to "one embodiment" or to "an embodiment" means that a particular feature, structure, or characteristic described in connection with the embodiments is included in at least one embodiment. The appearances of the phrase "in one embodiment" or "an embodiment" in various places in the specification are not necessarily all referring to the same embodiment.

Some portions of the detailed description that follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations or transformation of physical quantities or representations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device (such as a specific computing machine), that manipulates and transforms data represented as physical (electronic) quantities within the computer system memories or registers or other such information storage, transmission or display devices.

Certain aspects of the embodiments include process steps and instructions described herein in the form of an algorithm. It should be noted that the process steps and instructions of the embodiments could be embodied in software, firmware or hardware, and when embodied in software, could be downloaded to reside on and be operated from different platforms used by a variety of operating systems. The embodiments can also be in a computer program product which can be executed on a computing system.

The embodiments also relate to an apparatus for performing the operations herein. This apparatus can be specially constructed for the purposes of the operations (e.g., a specific computer) or it can comprise a general-purpose computer selectively activated or reconfigured by a program stored in the computer. Such a computer program can be stored in a computer readable storage medium, such as, but not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. The memory/storage can be transitory or non-transitory. Memory can include any of the above and/or other devices that can store information/data/programs. Furthermore, the computers referred to in the specification can include a single processor or can be architectures employing multiple processor designs for increased computing capability.

The algorithms and displays presented herein are not inherently related to any particular computer or other apparatus. Various general-purpose systems can also be used with programs in accordance with the teachings herein, or more specialized apparatus can be constructed to perform the method steps. The structures for a variety of these systems will be clear to the skilled artisan based on the description provided herein. In addition, the embodiments are not described with reference to any particular programming language. It will be appreciated that a variety of programming languages can be used to implement the teachings of the embodiments as described herein, and any references below to specific languages are provided for disclosure of enablement and best mode.

In addition, the language used in the specification has been principally selected for readability and instructional purposes, and cannot have been selected to delineate or circumscribe the inventive subject matter. Accordingly, the disclosure of the embodiments is intended to be illustrative, but not limiting, of the scope of the embodiments, which are set forth in the claims.

Apparatus of the Invention

In one embodiment, an apparatus for amplification of a nucleic acid in a sample is disclosed. The apparatus comprises a semiconductor substrate, a temperature sensor, a light sensor and a biocompatible coating deposited over the substrate and the other components. In a related embodiment, the apparatus comprises a heating element. A sample along with reagents for a polymerase chain reaction (PCR) is deposited on the substrate and instructions provided by a processor direct heating and cooling of the sample by the apparatus. In one embodiment, amplification of nucleic acid in a sample is detected by the light sensor formed on the substrate.

Substrate

The apparatus includes a semiconductor substrate. A semiconductor substrate is a solid substance with limited electrical conductivity, which can be modulated by adding impurities—a process known as doping. Examples of semiconductor substrate materials include but are not limited to silicon, germanium, gallium arsenide etc. In one embodiment, the semiconductor substrate is a planar surface onto which electronic devices or components are formed through pattered diffusion of doping elements. The electronic components can also be interconnected to each other with metal traces deposited on the surface of the substrate. The process steps to form electronic components on semiconductor substrate typically include deposition, etching, photolithography and ion implantation, etc.

Over the history of development of semiconductor manufacturing processes, certain types of processes became particularly popular and advanced. These are optimal for forming circuits that give rise to the main stream integrated circuit products such as microprocessors, networking and communication processors and controllers, industrial and automotive controllers etc. A good example of such process is the complementary-metal-oxide-semiconductor process or CMOS. Due to this advancement, it is possible to manufacture highly integrated, highly functional systems on a silicon chip at very low unit cost.

Temperature Sensor

Figure 5:
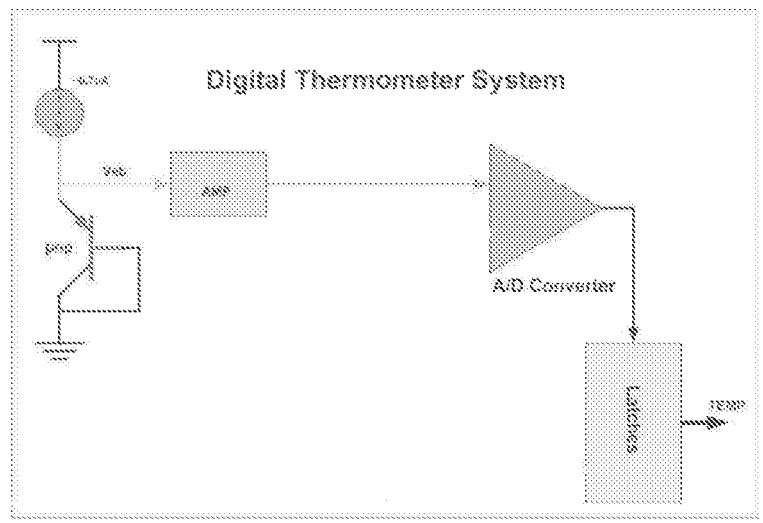
FIG. 5 shows a temperature sensor based on a PNP type of bipolar transistor. The Emitter to Base Voltage (Veb) is amplified, digitized and stored in a digital register (shown as "Latches") for access by a microprocessor or other types of digital circuits.

The apparatus includes a temperature sensor formed on the substrate. A temperature sensor is a device that measures temperature and converts it into a signal, which can be read by another device or component. Many circuit components, such as a bipolar transistor, have operational properties that are affected by temperature. A temperature sensor is thus a circuitry that utilizes this property and converts temperature to an electric signal. An example of such a temperature sensor is shown in FIG. 5. The temperature sensor is based on measuring the Emitter-Base voltage of a PNP type bipolar transistor. The measurement is amplified, converted from analog to digital, and represented in a digital latch that is readable by a microprocessor.

The temperature that is measured by the temperature sensor described herein is the temperature at the junction of the temperature-sensing transistor, or junction temperature. Because semiconductor material, such as silicon, has very low heat capacity, or very high heat conductivity. The junction temperature can be used as a fairly accurate representation of the temperature of the entire chip and the small amount of liquid sample deposited on the chip. Thus the measured temperature represents the temperature or a change in temperature of a sample deposited on the apparatus.

The temperature sensor can detect the temperature periodically, at a predetermined frequency or responsive to instructions provided by a processor. Similarly, the temperature sensor can report the detected temperature to another device at a periodic interval or when a change in temperature is detected. In one embodiment the temperature sensor provides the temperature information to a processor.

Heating Element

The apparatus includes a heating element formed on the semiconductor substrate. In one embodiment, the heating element can be a transistor or a resistor.

All electric components will consume power and generate heat to some degree. In a typical semiconductor chip design, an effort is made to minimize heat dissipation inside the chip. This is achieved through careful design such that the switching elements (i.e., transistors) are either fully open (off) or closed (on). In the former case, the current flowing through the transistor vanishes; in the latter case, the voltage drop on the transistor is zero. It is assumed there is a "load" between the power and the transistor, and in this case, the entire voltage drop occurs on the "load", not the transistor.

Figure 6:
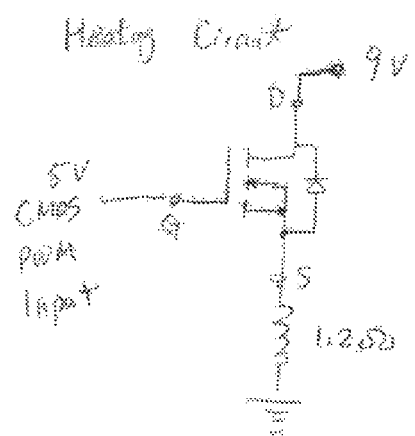

In the present invention, the transistor, when configured as a heater, is purposefully designed to generate heat in a controlled fashion. Transistors may be partially turned on, allowing current to flow through and, at the same time, allowing voltage to drop across the current path. In this way, the transistor consumes power and generates heat. A transistor configured to function this way can be a power MOSFET transistor configured with a resistor placed in between SOURCE and GROUND (FIG. 6). In this example, the input to the GATE of the transistor can turn the heater on and off. A typical method to modulate the heat element is through pulse width modulated input signal, or PWM.

It is also worth noting that in designing such a heating element, the transistor can be sized based on the amount of power it can consume and convert to heat. This ensures that physical damage does not occur during operation.

The advantages of using transistors as heating elements are twofold. First of all, transistors are easy to fabricate on semiconductor substrate. The operating parameters of transistors are relatively easy to control during the fabrication process relative to many other components (e.g., resistors). This facilitates device-to-device uniformity. Secondly, in operation, transistors can be easily and quickly turned on and off by other circuits, such as a microprocessor. This means that the amount of power consumed to generate heat can be easily modulated in real time, for example, using a pulse width modulation (PWM) method.

It is also possible to generate heat by passing current through resistors on the chip. The semiconductor manufacture process allows forming of resistors on the semiconductor substrate. These resistors can be either metal or poly silicon. Sometimes, a resistor is formed using the same technique for forming transistors.

Light Sensor and Noise Reduction Circuit

The apparatus includes a light sensor formed on the semiconductor substrate. The light sensor is made of one or more circuit elements called active pixels. A pixel consists of a photodiode and a read out circuitry. A photodiode is a specially formed semiconductor component that converts photon influx to electric current. Examples of such components are reverse-biased PN junction photodiode and the P+NP pinned diode, as shown in FIG. 7. The read out circuitry, which consists of 3 to 4 transistors, integrates photo diode current into a voltage that can be amplified and read. The light-to-electric conversion can be controlled to start at a desired time and last for a prescribed period of time, much like the shutter of a camera. Many pixels can be formed and laid out into an array, providing image sensing capability.

In molecular biology, one of the most robust methods to identify a target of interest is to label the target molecule with a light-emitting substance, e.g., fluorescence-emitting compounds or bioluminescent compounds. Under light stimulus, a fluorescent-labeled molecule will absorb the energy from the stimulus light and then emit light at a slightly longer wave length. Sometimes there is also a small time delay between light excitation and emission. The difference between the two wavelengths is referred to as the Stokes shift. This property is the basis of separation of emitted fluorescence from excitation light. In the case of bio-luminescent probes, no excitation light is needed. Light signal is generated as a result of chemical reactions.

For example, fluorescein amidite fluorophore or FAM (a typical a fluorescent dye) has an excitation wavelength of 492 nm. This is the wavelength at which it can be most efficiently excited by excitation light. When the fluorophore is excited, it will emit light at a center wavelength that is different from the excitation wavelength. The emission wavelength is usually longer than the excitation wavelength. For FAM, the emission wavelength is centered on 518 nm.

In fluorescence detection, to be able to separate excitation light and light emission is important since the strength of emitted light is much less than that of the excitation light. A preferred method to achieve this separation is to use filters that selectively filter out light of a given wavelength range. For FAM, a filter that can filter out wavelengths shorter than 505 nm can effectively block the excitation light, while allowing the emitted light to pass. The emission filter is preferably a bandpass or long pass filter whose cut off frequency is somewhere midway between the peak excitation wavelength and peak emission wavelength. It is often desirable to be able to sense multiple fluorophores in the reaction mix, fluorophores with distinct excitation and emission wavelength are selected. For example, the fluorophore ROX has the center excitation wavelength of 578 nm and peak emission wavelength of 604. To sense more than one fluorophores, such as FAM and ROX in the same reaction mix, multiple excitation light sources with different filters are used, each suitable for the intended fluorophore. For example, a green LED with an excitation bandpass filter whose center wavelength of 578 is used for ROX. The excitation light sources are typically turned on alternatively or sequentially. On the detector side, different wavelength filtering characteristics are built into the system. For example, we would "pattern" the filter such that different portion of the filter would have difference wavelength characteristics, e.g., center wavelength and cut off wavelengths for a bandpass or long pass filter. In such a way, different light sensors are subject to different filtering effects and the pixels can preferably sense light of different wavelengths. As explained before, a bandpass filter with center pass band wavelength of 518 nm is suitable for FAM, whereas a bandpass filter with center pass band wavelength of 604 nm is suitable for ROX.

Even though different fluorophores have different emission wavelengths, their emission wavelength ranges overlap. As a result, signal cross-talk can be an issue. For example, consider FAM (peak emission wavelength of 518 nm) and ROX (a peak emission wavelength of 604 nm) and corresponding light detectors A and B with sensitivity ranges of 518 nm+−30 nm and 604 nm+−30 nm, respectively. Detector A is used to detect FAM and detector B is used to sense ROX. However, sensor B will still produce a weak response in the presence of FAM only. One way of interpreting the responses is to employ the method where is alternately excited by light sources intended for FAM and ROX, followed by comparison of the responses of sensor A and sensor B. If the signal generated by sensor B increases when the excitation light source optimized for ROX is used, then ROX is likely present. Conversely, if sensor B response decreases when the excitation light source optimized for ROX is used, then sensor B response is likely cross talk from FAM.

The major challenge associated with detection fluorescent light from molecular marker using semiconductor sensor is in detecting very low level of light. Semiconductor photo detectors are generally noisy. In the context of fluorescent detection in molecular biology, the inherent noise of the photo detector can be as much as 10 times higher than the detected signal. Thus methods to enhance photo-detector signal to noise ratio (SNR) are critical.

The noise carried by a photodetector is often referred to as dark current by practitioners in this field. The dark current typically contains two portions. There is a "fixed" portion that is time invariant for a given photodetector when all other conditions, such as temperature, supply voltage, etc., are kept constant. The second portion of the noise varies over time and is random and unpredictable. This second portion of the noise is often called "shot noise."

In order to cancel out the fixed portion of the noise, the following techniques are used. Since it is know that fluorescent emission is caused by optical excitation, and optical excitation timing and duration is controlled by the same processor responsible for detection, repeated samples of the photodetector signal are taken before optical excitation is applied. These are samples called "dark frames". The output of these samples is then averaged and used as the estimate of the fixed portion of the noise. This estimate can then be subtracted from light measurement when excitation is applied to eliminate the fixed portion of the noise.

In order for the estimation of fixed noise to be accurate, we make sure that the operating conditions for taking dark frames are exactly the same as the conditions for taking normal samples of fluorescent emission when optical excitation is applied. For example, we would take capture the dark frames, as well as normal light frame during a time when the temperature is kept constant. As described elsewhere herein, there is a period of time during PCR, namely the annealing time, when the temperature is maintained precisely at a fixed level. It is also desirable to use the period of time when the temperature is the lowest to minimize noise. In PCR, it is the annealing time that the temperature is the lowest (typically between 55 degree C. to 65 degree C.).

To reduce the time-variant portion of the noise, or shot noise, we employ the method of repeatedly sampling, digitizing the photodetector outputs and averaging them. Since the shot noise for repeated samples is uncorrelated, the noise from multiple samples tends to cancel itself out. This can be done within a period of time when the operating condition of the chip is constant. For the same reasons described above, the annealing time is preferred for applying the noise-reduction procedure. Note that the annealing time is in the tens of seconds, and occasionally over a minute, for each PCR cycle. Hence, relatively long periods of time exist to integrate photodiode current and take repeated samples to average out shot noise.

Since the ultimate goal is to increase the signal-to-noise ratio, efforts to increase signal strength are as important as the above-described efforts to reduce noise. In preferred embodiments of the apparatus and methods described herein, the bioassay is coupled directly to the sensor embedded in the semiconductor substrate such that the optical path is as short as possible and optical loss is kept to a minimum. Moreover, the detection area of the light sensor is designed to match the size of the reaction volume, thus maximizing the absorption of photon influx without the use of bulky focusing lenses. The pixel size of an image sensor customized for use in molecular biology may be larger than the image sensors used for cameras or camcorder. Larger pixels yield better signal strength.

For an array of light sensors, it is also possible to reduce the noise with circuitry that compares input from many densely packed sensors and then cancels out the noise. For example, although the properties of pixel circuitry can vary from individual pixel to individual pixel or from chip to chip, it is easier to make 2 adjacent pixels with matching properties. So in one embodiment, we have two adjacent and identically designed pixels working together. One of the pixels is permanently covered by a layer of metal or other material that prevents the passage of light. The differential output of the two pixels gives a better indication of light stimulus and free of some aspects of the noise introduced by the pixel circuitry itself. Pixels that are covered to provide estimated dark current for subtraction from normal pixel output are sometimes called "dark pixels".

Biocompatible and Wavelength Filter Coating

The apparatus comprises a biocompatible coating deposited over the substrate and integrated components. Numerous polymer-based materials are shown to be compatible with molecular biochemical assays such as those used for PCR. Examples include polypropylene, polyurethane, parylene, epoxy, and polycarbonate. Epoxy and parylene have been shown to function well in coating applications. Epoxy, for example, has been shown to be hydrophilic, which helps to promote contact of the assay with the chip surface and ensures optimal heat transfer.

Another important function of the coating is to filter incoming light by its wavelength. As mentioned earlier, the coating filters incoming light such that light emission with wavelengths shorter than a given value is blocked. This kind of filtering is called a long pass filter. Wavelength filtering is achieved through thin film coating. An example of such coating is composed of alternating layers of two or more dielectric materials of different refractive indices, such as zinc sulfide (refractive index of 2.35) and cryolite (refractive index of 1.35). FIG. 8 illustrate this concept.

As widely known to practitioners in the semiconductor arts, integrated circuits are initially formed on a disc-shaped substrate called a wafer. Many instances of the chip, which are rectangle in shape, are repeated on the wafer. After the wafer is fully processed, it is then cut and individual chips are obtained. It is important that application of the coating is done at the wafer level, instead of to each chip. This method is both more economical and results in a better quality chip.

Applying the coating mentioned above may introduce surface tension in such a way that it can cause the wafer to bend and deform. One method to address this problem is to apply coatings on both side of the wafer to counter balance the tension and ensure the structural integrity of the wafer.

An alternative method of adding a filter is to laminate a layer of filter made of coated glass, quartz or polymer (examples of transparent polymers are polycarbonate, polypropylene) on top of the semiconductor substrate. In this case, using glass as example, the filter is made by applying coatings onto a glass wafer. The glass wafer is then cut into individual dice about the same size as the silicon chip. The glass filter die is then bonded to the silicon chip die.

Solid Support

Semiconductor substrate or chip typically does not have the structure integrity to form a standalone functional device. It is always desired to package the semiconductor chip on to a supporting structure. In this invention, the semiconductor chip rests on and is bonded to a solid support. A typical such support is a printed circuit board that has metal conductor traces etched onto it. The semiconductor chip makes electric contact with the metal traces of the circuit board through bonding wires.

Temperature Controller

The purpose of the temperature controller is to adjust the inputs to the heating element to make the actual temperature, as measured by the temperature sensor to match a desired temperature level called the temperature set point. The temperature controller compares the reading from temperature sensor and a set point. A control algorithm implemented in the temperature controller translates the difference into inputs to the heating element to make the output temperature match the set point. Proper choice of the control algorithm ensures the actual temperature reaches the temperature set point quickly without overshooting the level defined by the set point. The controller typically combines the proportional, integral and differential aspects of the temperature measurement to set point difference to generate inputs to the heating elements (i.e. the actuators), as in PID control.

Several aspects of this design ensure high quality temperature control. First of all, the semiconductor substrate has very low heat capacity. Along with the fact that the amount of fluid being assayed is very small, this means that the temperature changes quickly with heating or cooling inputs. A mechanical analogy of this kind of system is one that has very low "inertia". Moreover, heating elements such as MOSFET transistors with pulse width modulated inputs act very quickly. The combined effect means the actual temperature can very accurately and quickly match the temperature set point.

Timers

Part of the logic circuitry integrated on the chip may include one or more timer devices. A timer is a logic circuitry that can be programmed to measure elapsed time and generate interrupts to the CPU. A timer is fed a clock source as the timing base. The clock is a square wave logic signal with very stable period. For example, a timer can be a counter that counts clocks. Furthermore, a timer can be programmed to count a desired number of clocks. If the timer counts a prescribed number of clocks, it either raises a flag, causing a register bit to go from '0' state to '1' state that can be polled by the CPU; or generates interrupts to the CPU. An application program can use said timer to time events or schedule actions.

A stable clock source is used for the operation of the timer. In fact, a stable clock source is used for many other digital circuits such as the CPU. This clock can be fed from outside of the chip, or generated internally with an embedded oscillator circuitry. In this case, since the chip is connected electrically to the instrument, it would be easy to let the instrument supply the clock source. Stable clocks can be generated from many well known electronic circuits and components that are based on Quartz (crystal) or MEMS oscillators.

An additional array of programmable counters, known as PCA (programmable counter array) can be employed to provide pulse width modulated (PWM) inputs to the heating elements. The CPU can decide the frequency and duty cycle of pulse width modulated signals as a means to control the input signal strengths to the heaters.

Temperature Cycling Control with the Help of a Timer

To enable PCR, the semiconductor chip will generate and control the heat to cause the assay fluid to cycle through different temperatures levels at prescribed time periods. Typical cycle temperatures and timer periods are shown in Table 1.

TABLE 1

Exemplary PCR temperature cycling schedule

| 30-40 Cycle | 94-95 degree C. | 30 sec | Cooling down time: 14 s |
| --- | --- | --- | --- |
| | 55-58 degree C. | 30 sec-1 min | Heat up time: 10 s |
| | 72 degree C. | 1 min | Heat up time 10 s |

In one embodiment, the temperature cycling control is managed by a microprocessor, described elsewhere herein. The microprocessor can decide the set-point of the temperature feedback control loop as a way to set the desired temperature of the chip.

In another embodiment, multiple samples of assay fluid are housed in separate chambers on top of the chip. In this design, multiple "sites" exist on the chip for each of the samples. Each site will have its own temperature sensor, heater and temperature control systems. These temperature control systems can be controlled by the same processor in a time sharing (or time slicing) fashion. With this method, assuming the temperature set points are the same across the sites, better temperature uniformity can be achieved.

Analog to Digital Converter (ADC)

In a preferred embodiment of the apparatus, one or more analog to digital converters (ADC) are formed on the substrate. These converters convert analog information produced by the sensors to digital information for efficient communication and further processing by the processor.

Various ADC architectures exist. Some are fast but have low resolution, e.g., a flash ADC. Some are slower but have higher resolution, e.g., successful approximation ADCs, single slope ADCs and dual slope ADCs. Another class of ADCs use over-sampling to achieve high resolution at the cost of high switching noise, e.g., sigma-delta ADC. Preferred embodiments use single slope or dual slope ADCs1

When the apparatus communicates with the external read out device, on-chip ADCs enable such communication to be carried out digitally. Various error control and correction methods made possible with digital communication, e.g., parity check, cyclic redundancy check, resend mechanism, etc., further improve the reliability of operating this apparatus for clinical or point-of-care use. Although some aspects of noise produced by the sensors can be filtered out in analog domain, processing the sensor information digitally to remove noise is preferred. In preferred embodiments, the ADCs are close to the sensors. In some embodiments, where filtered sensor information is processed to control the reaction or to produce final diagnostic results, that filtering is also performed digitally.

Processor

In a preferred embodiment, a microprocessor is formed on the chip. The processor executes instructions stored in memory and carry out control, sensing, and communication tasks that are defined in the instructions or programs stored in memory.

Most of the special function circuitry on the chip, such as the heating elements, temperature and image sensors, and communication controllers are directly controlled by the processor to perform their tasks. In other words, the inter-working of these components is managed by the processors according to the instructions in the computer programs stored in memory. This results in maximum flexibility and programmability, and architectural simplicity. For example, in temperature control, the processor receives the temperature information from the temperature sensor, along with information from other components such as the timer and provides heating and cooling instructions to other components of the apparatus and outside the apparatus to heat and cool the sample. The heating and cooling instructions can be used to perform a polymerase chain reaction (PCR) to amplify a single or a few copies of a piece of DNA.

In one embodiment, the processor can be provided on the semiconductor substrate. In other embodiments, the processor can be housed in another device separate from the semiconductor substrate.

Memory

In a preferred embodiment, various types of memories are embedded on the chip. The memories are used to store code and data for use by the embedded microprocessor. This is rather common for semiconductor chips containing embedded processors. In an exemplary implementation, a portion of the memories is non-volatile. Non-volatile means that the content of the memory is retained when power is off. Non-volatile memory can be read only memory (ROM), OTP memory (one time programmable memory), EEPROM or flash (many-time-programmable non-volatile memory). Nonvolatile memory is a convenient location for storing start up, bootstrap code, loader programs, calibration data etc.

Moreover, when PCR reagents are pre-packaged in the device, it is preferred that information about the reagents is stored in the non-volatile memory. Furthermore, the parameters for the PCR reaction, such as target temperature and time periods, relate to the particular PCR reagents used and may therefore also be stored in non-volatile memory. At the time of the reaction, the operator is no longer required to input the reaction parameters. Instead, he/she is only required to add sample, insert the device, and push one start button to commence the PCR reaction.

The content of RAM memory is lost when power is off. On power up, the content of the RAM memory is uninitialized. RAM memory can be used to store temporary data, or program code in normal operation. The program code stored in RAM memory can be loaded from the external device through the communication interface, or from on-chip non-volatile memory.

Cartridge Housing the Apparatus

In a preferred embodiment, the semiconductor chip is part of a cartridge apparatus containing one or more chemical reagents necessary for the amplification and detection of nucleic acid. One or more chambers are formed inside the cartridge, where the bio-chemical reagent is stored during the reaction. The semiconductor chip forms at least one surface of this chamber, in such a way that the fluid is in direct contact with the semiconductor chip surface coating layer. This allows the chip to directly heat the sample, as well as sensing the temperature of the sample. By allowing the biochemical reagent fluid to come into direct contact with the chip, it is also possible to allow light emission from the sample to pass to the light sensors of the chip with minimal optical loss.

In one embodiment, at least one of the walls of the chamber is optically transmissive, allowing excitation light to pass through this wall and incident on the reagent mixture, to excite fluorophores. In a preferred embodiment, the direction of excitation light is chosen such that the excitation light does not incident on the sensor surface directly. Preferably, the direction of the excitation light should be perpendicular to the normal of the light sensor surface, i.e., the semiconductor chip.

For each chamber housed inside the cartridge, there is at least one opening for injecting the sample and reagent into the chamber. In one embodiment, a second opening for a chamber, such as a vent is also provided. Having a second opening as a vent helps to prevent the formation of bubbles inside the chamber. During the reaction, these openings may be covered or sealed to prevent evaporation.

Figure 10A:
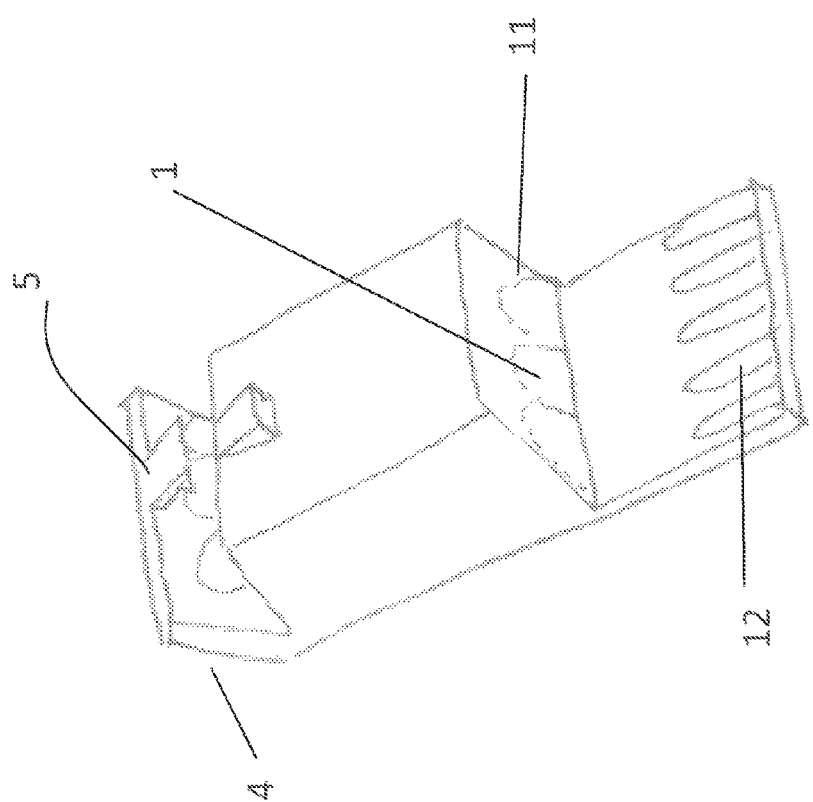
FIG. 10 shows a preferred embodiment of the PCR cartridge apparatus (10a is a perspective view; 10b is a side view; 10c is a frontal view). In this design, the semiconductor chip is oriented vertically. The optically transmissive wall forms the bottom wall of the chamber. The inlet and outlet openings are placed on the top of the chambers Legend: 1, chambers; 2, Inlet; 3, Outlet; 4, Cap; 5, latch; 6, semiconductor chip; 7, socket; 8, PCB board; 9, LED; 10, excitation filter; 11, transparent window; 12, electric contact.
Figure 10B:
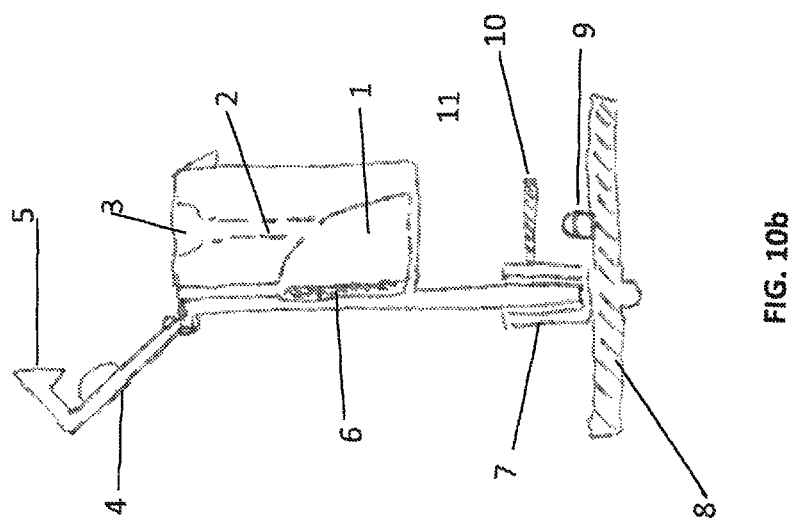
Figure 10C:
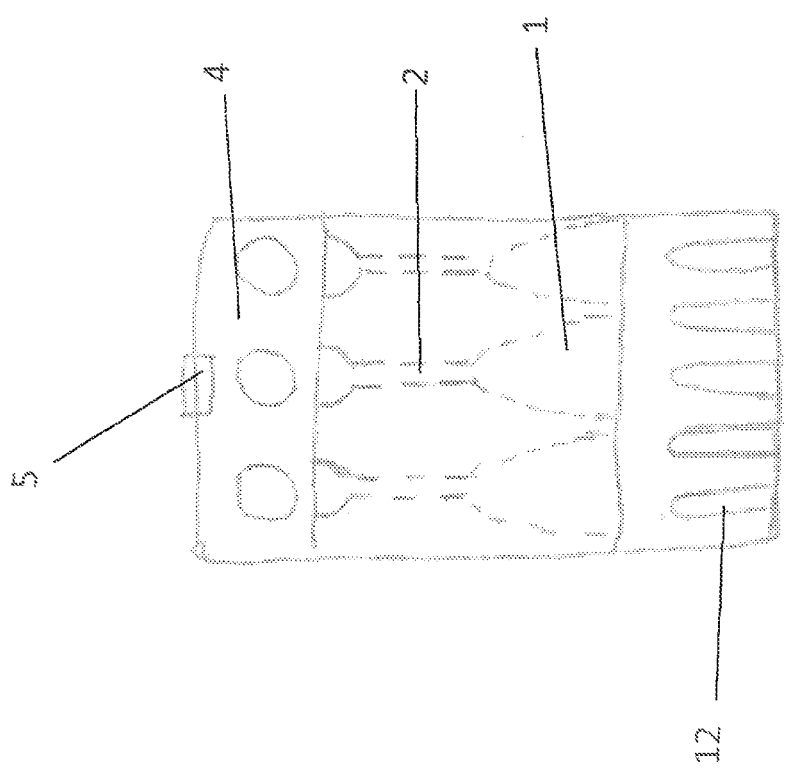

The semiconductor chip acts as the heating plate for the sample housed inside the chamber. The chip surface may be vertical, horizontal, or tilted relative to gravity. A tilted heating surface may prevent uneven heating due to internal fluid circulation. In a preferred embodiment, the semiconductor substrate and heating surface is oriented vertically. The optically transmissive wall forms the bottom wall of the chambers. In a related embodiment, inlet and outlet openings are present at the top of the chambers. The chambers may be arranged in a row horizontally (see FIG. 10) and coupled to the light and temperature sensors of the semiconductor chip.

A typical PCR-based analysis involves running multiple samples under identical conditions. At least one sample is designed to amplify and test a target nucleic acid, such as nucleic acid extracted from a pathogen (e.g., viruses or bacteria). Other samples serve as negative or positive controls, or they may simply repeat the test sample reaction. Such a design helps ensure that what is detected is from the target samples, and not an artifact. In order for this method to work, it is important that all conditions—temperature, timing, and sensitivity of the light detectors—are identical across the samples.

The invention described herein helps facilitate sample-to-sample uniformity. A single integrated circuit semiconductor chip today may contain many functional components which can be formed and tuned such that they have uniform operating parameters. Over the time scale of biochemical reactions such as PCR, these components operate in parallel at precise points in time.

For example, we can have multiple "sites" on the chip, each of which corresponds to a chamber housing the biochemical sample. Each site can have its own temperature sensor, heater and light sensor, and it can be configured and controlled to operate at exactly the same conditions, including temperature, timing of temperature changes and timing of optical detection.

In contrast, conventional PCR equipment attempts to achieve temperature uniformity by using highly heat conductive blocks to house the tubes. The temperature gradient inside such heating blocks is still significant, however, and undermines test results with multi-sample PCR. Moreover, in conventional PCR instruments, optical detection is performed serially across the samples. A motion control system is employed to move sample one by one into the optical path. The time difference introduced by a mechanical system is large enough to skew test results.

Another significant advantage of this invention is that the sample comes in direct contact with the optical sensor on the chip. This means minimal optical loss and maximum signal strength. Since all light sensors are noisy, higher signal strength means higher signal to noise ratio and therefore higher sensitivity of the whole instrument.

To summarize, the invention described herein gives rise to a PCR system capable of achieving the highest sensitivity with optimum sample-to-sample reproducibility. These two characteristics are the most important performance parameters of a PCR system. Furthermore, this result is obtained at significantly reduced cost.

Other Variations of the Cartridge Design

We described earlier that the cartridge can house multiple chambers, and these multiple chambers can be formed on top of the same semiconductor chip. It is preferred that these chambers are segregated, in that the reagent fluid contained in these chambers will not mix. The nucleic acid molecules to be amplified are usually uniformly suspended in the fluid. However, other variations of fluidic design may be used for different application needs.

In certain embodiments, reagent mixtures introduced into the chambers may contain magnetic beads. These magnetic beads generally have diameters ranging from 1 µm to 500 µm, with nucleic acid probes or fragments covalently bonded to the surface of the beads. The use of magnetic beads to capture and immobilize nucleic acids and proteins is well known in the art. For DNA capture, magnetic beads that are coated with silica, Streptavidin, COOH are shown to be effective.

An external magnetic field can be introduced to the vicinity of the cartridge to immobilize the magnetic beads, so that when fluids are introduced or removed from the chambers, the magnetic beads and the molecules attached to the beads remain in the chamber.

One or more open wells can be formed on the surface of the chip, so that under the influence of external magnetic fields, the magnetic beads will be immobilized within these wells. Moreover, the size of the wells and magnetic beads can be chosen such that only a single magnetic bead falls into each chamber.

The interaction between nucleic acid molecules in the reagent fluid and the probes on the magnetic beads can cause emission of light, due to fluorescence or bio-luminescence. Such light emission can be detected by the light detectors formed on the semiconductor chip. Individual light sensor pixels may be formed under the wells such that the magnitude and time of light emission from individual wells can be specifically detected and measured.

In another embodiment, the molecular probes can be covalently bonded or attached directly to the surface of the semiconductor substrate with its layer of bio-compatible coating. Since different probes are attached to different pixel areas on the substrate, the sensors can sense the different activities of the theses probes.

Sealing of the Chambers

During the PCR reaction, the chamber may be sealed to prevent the fluid from expanding, evaporating or escaping the chamber. In one embodiment, the chamber openings can be reversibly covered by a lid or cap. The cap can be made of a polymer with some elasticity to allow a proper seal when a certain amount pressure is applied. The cap can be held with a set of latches to apply and maintain the pressure (illustration FIG. 10). In another embodiment, a pressure-activated one-way check valve can be formed inside the channel which forms the openings to the chambers. In yet another embodiment, the chamber openings can be sealed with an oily compound or immiscible liquid, e.g., mineral oil.

Communications Device

The removable cartridge may communicate with an external instrument device and exchange various information, e.g., the status of reactions and the results of measurements. The cartridge may also receive high-level commands from the external instrument which is equipped with user interface features, e.g., a keypad and display. High-level commands include those that instruct the cartridge device to start or terminate reactions. Certain features and functions that are necessary for the reaction, such as assisted cooling and optical excitation, may also be carried out by the external instrument device. In that situation, the processor in the cartridge would send instructions to activate and modulate these functions.

A 2-way communication interface is established between the cartridge and the instrument, and implemented over the electric contacts between the cartridge and the instrument.

To simplify the electric connection and minimize the number of contacts, the communication is best handled by a serial communication interface. Serial communication between two chips, the semiconductor chip and the main processor in the instrument, is well known. There are a lot of industry standard protocols for this type of communication. A well established and suitable protocol is the RS232. Another similarly suitable standard is the serial peripheral interface, or SPI. Both use a controller on each side to translate between serial data stream and parallel data interface with the CPU. The RS232 communication controller is usually called a UART (Universal Asynchronous Receiver Transmitter) and SPI controller is simply called the SPI controller.

In digital communication, error checking methods such as parity check or cyclic redundancy check are typically used, in conjunction with a resend mechanism. This set of methods makes it possible to communicate more reliably to the outside circuits of the read-out instrument device even in a harsh environment where electric noise or imperfect electric contacts might otherwise prevent communication and proper functionality External Device The solution provided by this invention also includes an external instrument device with user interface features and network connectivity. The external instrument device can be either a handheld device or a small bench top device. This is shown in FIG. 1. The external instrument device has a socket to which the cartridge apparatus plugs in. The socket includes a multi-contact electric connector that allows the cartridge to be electrically connected to the external interface. This socket allows the cartridge to be inserted or removed.

One of the main functional features of the external instrument device is a user interface for human operators. The user interface features typically include a key pad and a display. Through this user interface, the human operator can initiate, monitor, control, suspend or terminate the reactions.

Moreover, the external instrument device can be connected to the outside world through a network interface. The advantages are numerous. In one embodiment, a wired or wireless networking controller and interface is included in the device. This allows the device to be connected to the Internet. The physical connections can be Ethernet, USB or Wi-Fi. The external instrument device can also have a build in wireless radio for connection to cell phone networks such as GSM or 3G networks, to achieve even better networking coverage. This allows the software running on the external instrument device to communicate to programs that reside elsewhere on the Internet.

The benefit of having network connection is particularly important when the invention is used as a disease diagnosis tool. The cartridge and instrument described herein can detect the nucleic acid in a sample. This capability alone is often not sufficient to perform a diagnosis result. Proper diagnosis can involve a much larger database stored somewhere else and accessible through Internet. In one embodiment, the sensor information obtained from the cartridge and instrument device is transmitted through Internet to a program running in a central server, having access to a large disease database. It is this program residing in the "cloud" that performs the disease diagnosis. The result of the diagnosis is subsequently transmitted back to the instrument device through the same Internet connection.

In another embodiment of the scenario, the Internet connection also (or alternatively) allows sensor data to be transmitted to a program running on the Internet which gathers and tracks information about disease status from various locations, e.g., as part of a regional or global epidemic control program. Information about the spread of diseases and the genetic composition of the pathogens can also be made available to drug companies as the basis to design and synthesize antibiotics and other forms of medical solutions.

The electronics of the external instrument device typically include a processor, different types of memory drivers and interfaces for the displays, keypad, network interface, radio, power management, and/or clock generator circuits, etc., much like a typical cell phone.

The external instrument device is a powered device. It derives power from the combination of sources, including onboard battery or external power supply, or both. Power management circuitry is included to manage power supply. Exemplary functions of the power management circuitry include battery level monitor and low power warning, battery level indicator, battery charging circuitry, and regulators to generate stable voltage supplies to internal circuitry.

The external instrument device also includes a communication interface to the cartridge device mentioned in earlier chapters for amplification and detection of nucleic acid. This is a wired interface through the electric contacts in the socket. The external instrument device also provides power and clock sources to the cartridge device.

In one embodiment, cooling and/or optical excitation functionalities are implemented in the external instrument device. For assisted cooling, a fan can be employed to create controlled airflow to the cartridge through the socket. A solid state cooling device, such as a Peltier device, can be used alone or in conjunction with the fan to provide the assisted cooling function to the cartridge. Optical excitation can be realized with one or more high power LED or laser diode housed in the external instrument device. An optical path that includes at least a transparent opening on the cartridge allows the optical excitation to act on the samples in the cartridge. LEDs have broad spectrum and are used together with the excitation filter described herein to provide band limited excitation light.

Factory Calibration

As in any instrument device, calibration is important to achieve precision. Typically, the instrument can be calibrated one or more times during the manufacturing process. The instrument can also be calibrated periodically during its life time. In one embodiment, calibration is automated by including a self-calibration program in each instance of the device.

Figure 9:
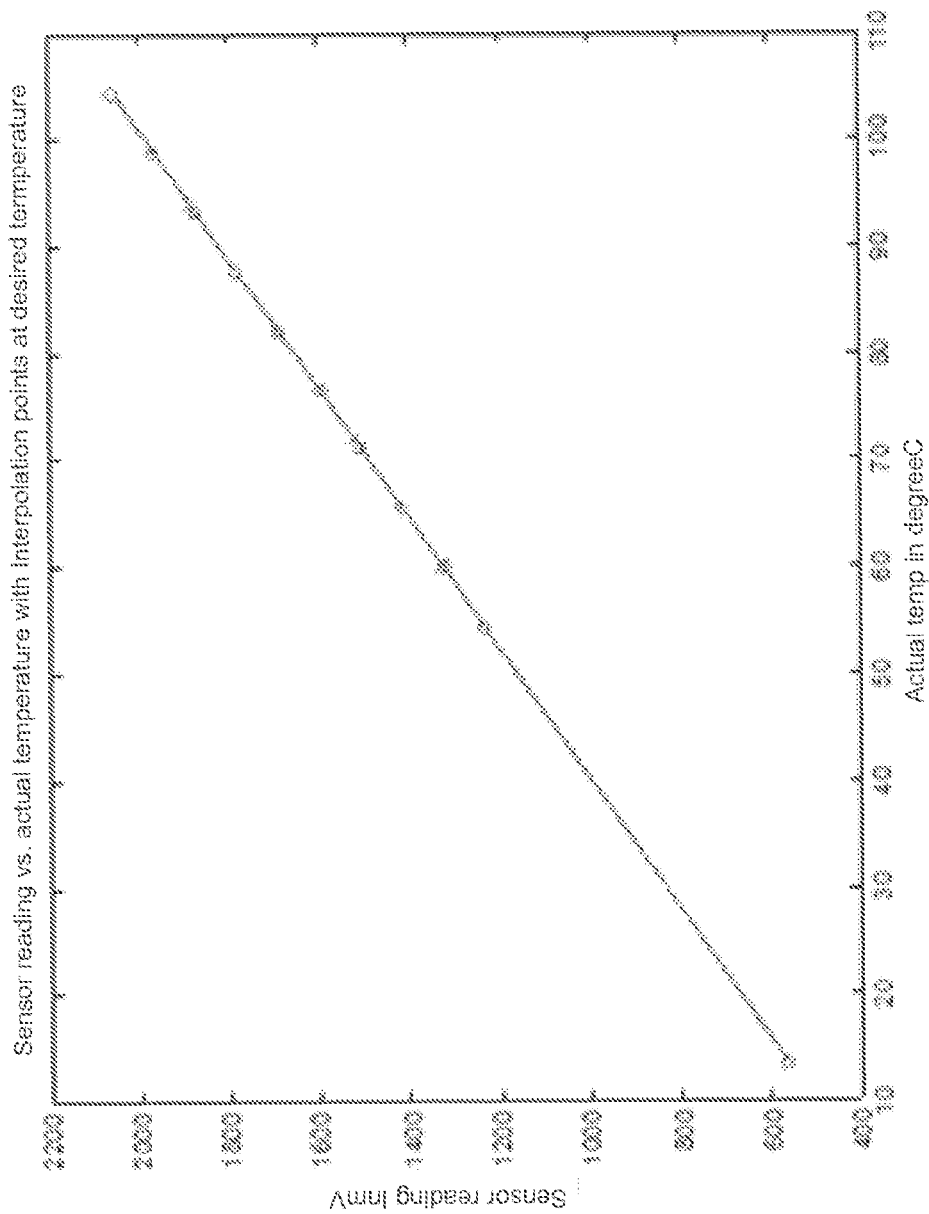
FIG. 9 shows a temperature calibration graph. To calibrate the temperature sensor, the chip is heated to a precisely controlled, known temperature and the output signal from the temperature sensors is read. Circles are points of forced temperature and measured temperature from a sensor. A curve fitting algorithm interpolates the data and establish the relationship between the sensor reading and the actual temperature. Crosses represent the interpolated temperatures at the points of interest, i.e., temperatures that will be used by the cycling program to amplify nucleic acid. The curve fit in this case embodies the correction factor between the sensor measurement and the actual temperature.

During factory calibration, the device is heated to a precisely controlled temperature level. The processor reads the inputs from the on-board temperature sensors and compares that with the actual temperature. If there is any discrepancy, a correction factor may be calculated and stored in memory for future use. The same process is repeated for many temperature levels covering the entire operating range of the device. FIG. 9 presents a temperature calibration curve.

Since the calibration program is stored on the chip and executed by the embedded processor, and since the result of the calibration is also stored locally in the memory of the device, the calibration process is fully automated. Moreover, it is possible to calibrate many devices in parallel. This is important for factory automation. Many devices can also be put on a board, typically called "burn in board", and go through the calibration process simultaneously in the factory, greatly improving throughput and reducing costs.

The same concept may be used for the calibration of light sensors.

Methods for Amplification of a Nucleic Acid

PCR

The cartridge and instrument device described herein may be used for a variety of biochemical reactions involving enzymes and optically labeled bio-markers. This is because most enzymes in biochemical reactions function at precisely controlled temperatures. A prominent example of such reaction is PCR, which is used to amplify and detect nucleic acids.

To prepare for PCR, the reaction sample is placed in the chamber housed in the cartridge through the openings. This can be done using a variety of dispensing instrument commonly available for such purposes, e.g., a manually operated pipette. PCR reagents typically include enzymes, nuclease-free water mixed with buffer, salts (e.g. $MgCl_2$), primers, nucleoside triphosphates and the target nucleic acid. The design and choice of primers is dependent on the target nucleic acid sequence. Practitioners in the art generally posses this skill.

When the cartridge and instrument device described herein are used for disease diagnosis or prognosis, the target nucleic sequence of interest is extracted from the bio-samples collected from the subject (e.g., blood samples, sputum, throat swabs, saliva, etc.). The sample that contains the target nucleic acid of interest can be mixed with PCR reagents prior to dispensing to the cartridge. Alternatively, the PCR reagents can be pre-mixed and dispensed to the cartridge prior to dispensing the bio-samples containing target nucleic acid.

Generally, the cartridge can have more than one reaction chamber containing pre-mixed PCR reagents with different combination of components. Some of these reaction chambers serve as negative and positive controls. For examples, before the reaction, one chamber can be dispensed with the target bio-sample, while a second chamber contains everything except the target nucleic acid of interest and serves as a negative control. After the reaction, if the first chamber shows a positive response and the second chamber does not, one would know, with higher level of confidence that the reaction result is not due to some artifact that is independent of the target bio-sample used in the reaction. A similar concept can be used to design positive controls. For example, a third reaction chamber can include a known concentration of nucleic acid template with matching primers. Where a negative result is obtained from the main reaction chamber and a positive result is obtained from the positive control chamber, it can be known with a higher confidence that the negative result from the main reaction chamber is due to the lack of target nucleic acid sequence in the sample.

The procedures of PCR have been described in U.S. Pat. No. 4,683,195 (Mullis) and U.S. Pat. No. 4,683,202(Mullis et. al.) To summarize, PCR involves repeated cycles heating and cooling. This process is called thermal cycling. The thermal cycle temperature and schedule is generally: phase 1—heat to 92 to 95 degree C. and maintain at this temperature for 30 seconds or so; phase 2—cool down to a temperature around 55 degree C. to 65 degree C. and maintain at this temperature for 30 sec to 2 minutes; phase 3—heat up to a temperature around 68 degree C. to 75 degree C. and maintain at this temperature for 1 minute or so; and then repeat. This sequence is typically repeated 30 to 40 times. For better results, the whole process usually starts with an extended phase 1, which is heating to and maintains at 92 to 95 degree C. for over 3 minute or so; and end with an extended phase 3, meaning heating to and maintain at 68 to 75 degree C. for over 10 minute or so. The exact temperature and periods depend on the target nucleic acid sequence and primer design. These choices are generally within the ordinary skill of a practitioner in the art.

During phase 1, a process called denaturation occurs, separating the two strands of the nucleic acid double helix. In phase 2, annealing occurs, in which the single-strand primers, comprising short chains of nucleic acid building blocks-adenine, cytosine, guanine, and thymine-bind to their complementary single-stranded bases on the denatured DNA. During phase 3, extension occurs; the polymerase enzyme synthesizes the nucleic acid, extending the single-stranded template that the primers started. This process converts one helix into two helices.

One variant of PCR is real time PCR. Real time PCR is a set of methods wherein the accumulation of PCR amplified nucleic acids can be monitored at real time instead of at end point. The cartridge and instrument device described in this invention supports real time PCR. In real time PCR, the amplified nucleic acid is made detectable using detectable label such as a fluorescent DNA-binding dye. Two common methods for detection of products in real-time PCR are available. In the first method, non-specific fluorescent dyes that intercalate with any double-stranded DNA are used. Because the amount of the dye intercalated into the double-stranded DNA molecules is typically proportional to the amount of the amplified DNA products, one can determine the amount of the amplified DNA by quantify the fluorescent emission from the sample. DNA-binding dyes that are generally useful for PCR include SYBR green, DAPI, propidium iodine, SYBR blue ethidium bromide and the like.

In the second method, sequence-specific DNA probes are labeled with a fluorescent reporter which permits detection after hybridization of the probe with its complementary DNA target. Since probe-based real time PCR replies on sequence specific detection of amplified DNA product, it results in more specific and sensitive detection. Probe-based quantitative amplification is described in U.S. Pat. No. 5,210,015 (Gelfand et. al.).

Fluorescent probes can be used in multiplex assays (e.g., for detection of several genes in the same reaction) by using sequence-specific probes with different-colored labels, provided that all targeted genes are amplified with similar efficiency. The method relies on a DNA-based probe with a fluorescent reporter at one end and a quencher of fluorescence at the opposite end of the probe. Breakdown of the probe by the 5' to 3' exonuclease activity of the Taq polymerase breaks the reporter-quencher proximity and allows unquenched emission of fluorescence, which can be detected after excitation with a laser. An increase in the product targeted by the reporter probe at each PCR cycle therefore causes a proportional increase in fluorescence due to the breakdown of the probe and release of the reporter.

In clinical diagnostics, the samples collected from the patient can be blood, serum, sputum, mouth swab, stool etc. These samples cannot be directly used in PCR reaction. A sample preparation step is needed to extract and purify the DNA molecules from the patient samples. The sample preparation process is necessarily carried out in separate container, vial, tube, vessel etc., which is different from the PCR reaction chamber we have discussed thus far. The conventional way of transferring the sample fluid from the sample preparation container to the PCR reaction chamber is to do it manually using a pipette. However, to facilitate point-of-care or clinical use, there are other preferred ways to transfer purified DNA from sample preparation container to PCR chamber. These methods are especially beneficial for applications involving samples containing infectious disease samples.

In one variation of the embodiment, the sample preparation chamber for extracting and purifying DNA from a patient sample (e.g., blood, stool, serum, sputum) is housed inside the cartridge. The sample preparation chamber is connected to the reaction chambers through channels, for example, two channels for each reaction chamber, one for transferring fluid, and one for venting. The purified DNA sample can be transferred to the reaction chamber through these channels. Extra pressure applied inside the sample preparation chamber may be needed to facilitate the transfer. Alternatively vacuum suction applied to the venting channels can also facilitate fluid transfer. Finally, valves formed inside the channels can be used to regulate the transfer.

Figure 11:
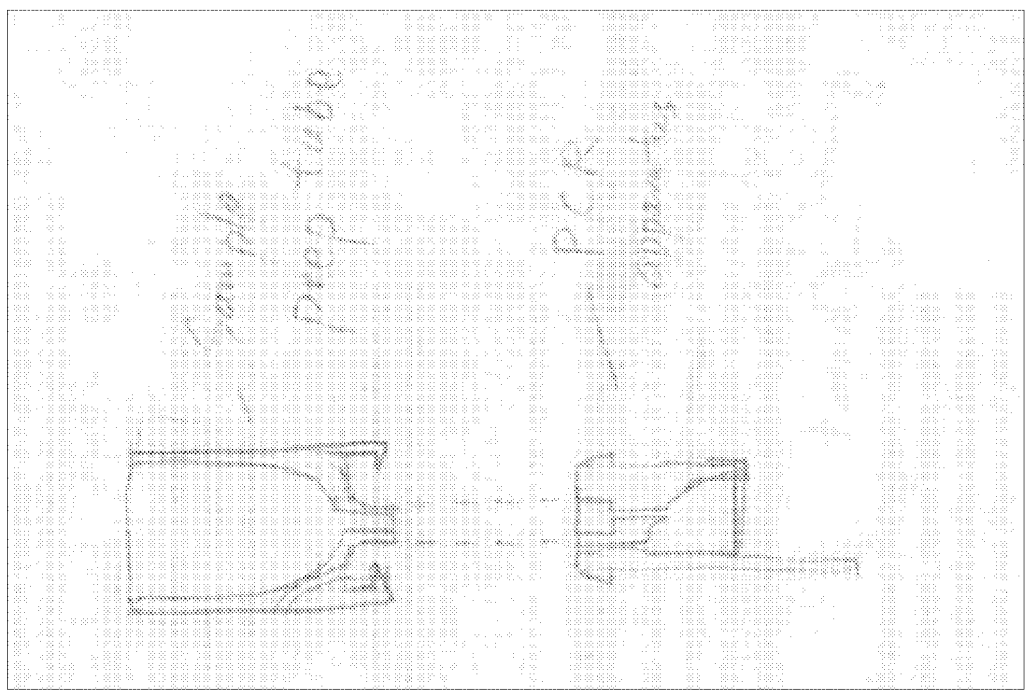
FIG. 11 shows an illustration of a method for transferring fluid from a sample preparation chamber to the PCR chamber.

In another variation of the embodiment, the sample preparation container can be a different apparatus. The sample preparation container can be mated or coupled to the PCR reaction chamber, allowing transfer of fluid with minimum chance for contamination. After the transfer, the two apparatus can be separated and then capped (see FIG. 11).

The reagents used for nucleic amplification and detection include such components as primers, reporter probes (e.g., Taqman probe), as well as template, buffer, polymerase, dNTPs, $MgCl_2$ etc. Some of these reagents, especially primers and probes, can be pre-stored in the reaction chamber in the factory, prior to the shipment and field use of the PCR apparatus. A preferred method of storing these components is to store them in a "freeze dried" or lyophilized state. Pre-packaging reagent components in lyophilized form eases storage and transportation. For example, lyophilized PCR reagents are known to be stable in the 2-8° C. range, whereas PCR reagents in liquid form typically require −20° C. storage temperature condition.

When the PCR apparatus is used for clinical diagnostics, the primers and reporter probes are specifically designed for the target diseases. Multiple primer sets and probes may be shipped with the device for separate dispensing into specific chambers of the device. These application-specific chemicals may be pre-packaged within the device to avoid human error and mix up in the field. A preferred embodiment is to prepackage PCR primers, probes in the reaction chambers of the cartridge prior to field use. Additionally, information about specific chemicals may be entered and stored in the non-volatile memory of the device and made accessible by the read-out instrumentation. Such information facilitates set-up and initiation of the reaction as well as post-reaction data processing.

At the field, the operator may still need to control the addition of other components to the reaction mix. Typically, these additional chemicals are generic (e.g., buffer, polymerase, dNTPs, $MgCl_2$) and not specific for each chamber, or each device. The chance of a mix-up will be minimal.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES CITED

U.S. Patent Documents

U.S. Pat. No. 4,683,195 A July/1987 Mullis et al.
U.S. Pat. No. 4,683,202 A July/1987 Mullis
U.S. Pat. No. 5,210,015 A May/1993 Gelfand et. al.

What is claimed is:

1. An apparatus for analyzing a biological sample comprising:
   a) a semiconductor substrate comprising an integrated circuitry,
      wherein the integrated circuitry on the semiconductor substrate comprises:
         a junction temperature sensor; and
         a first light sensor;
   b) a biocompatible coating over the semiconductor substrate,
      wherein the biocompatible coating is positioned to allow the biological sample to be in proximity to the integrated circuitry;
   c) one or more processors;
   d) memory storing one or more programs, the one or more programs configured to be executed by the one or more processors, the one or more programs including instructions for:
      detecting a first light input measurement from the first light sensor at a first time prior to triggering a light signal from the biological sample;

detecting a second light input measurement from the first light sensor at a second time after triggering the light signal from the biological sample;
   detecting a plurality of temperature input measurements from the junction temperature sensor,
      wherein the plurality of temperature input measurements comprises:
         a first temperature input measurement detected at the first time; and
         a second temperature input measurement detected at the second time;
   using the first light measurement to estimate noise signal; and
   using the plurality of temperature input measurements to further estimate noise signal and improve noise suppression, thereby determining the light signal from the biological sample.

2. The apparatus of claim 1, wherein the integrated circuitry on the semiconductor substrate further comprises a heating element.

3. The apparatus of claim 2, wherein the heating element comprises a transistor.

4. The apparatus of claim 2, wherein the heating element comprises a resistor.

5. The apparatus of claim 1, wherein the integrated circuitry comprises complementary metal-oxide-semiconductor circuitry.

6. The apparatus of claim 1, wherein the integrated circuitry further comprises a timer, wherein the timer is electrically connected to the one or more processors.

7. The apparatus of claim 1, wherein the biocompatible coating is hydrophilic.

8. The apparatus of claim 1, wherein the biocompatible coating is a light wavelength filter.

9. The apparatus of claim 8, wherein the biocompatible coating comprises a member selected from the group consisting of zinc sulfide, Cryolite, glass, quartz, and a transparent polymer.

10. The apparatus of claim 8, wherein the biocompatible coating comprises different portions with different light wavelength filtering characteristics.

11. The apparatus of claim 10, wherein the biocompatible coating is a laminate placed over the semiconductor substrate.

12. The apparatus of claim 1, wherein the biocompatible coating further comprises one or more nucleic acid amplification reagents deposited thereon.

13. The apparatus of claim 12, wherein the one or more nucleic acid amplification reagents comprises one or more magnetic beads, and wherein the one or more magnetic beads comprises one or more nucleic acid probes covalently attached thereon.

14. The apparatus of claim 13, further comprising a magnetic field generator positioned to immobilize the one or more magnetic beads on the biocompatible coating.

15. The apparatus of claim 12, wherein the location of the one or more nucleic acid amplification reagents corresponds with the location of the first light sensor.

16. The apparatus of claim 1, wherein the biocompatible coating comprises a sample partition, wherein the sample partition has a sample capacity, as measured by the amount of biological sample, of between 0.1 µl to 200 µl.

17. The apparatus of claim 16, wherein the sample partition is aligned with the first light sensor.

18. The apparatus of claim 1, wherein the integrated circuitry further comprises a digital communications device configured to communicate between the integrated circuitry and the one or more processors.

19. The apparatus of claim 1, further comprising:
   a communications interface;
   a user interface element; and
   a display.

20. The apparatus of claim 1, wherein the apparatus further comprises a cooling device.

21. The apparatus of claim 1, wherein the one or more programs further includes instructions for:
   heating the semiconductor substrate; or
   cooling the semiconductor substrate.

22. The apparatus of claim 1, wherein the one or more programs further includes instructions for:
   detecting a temperature input measurement from the junction temperature sensor;
   comparing the temperature input measurement to an actual temperature measurement; and
   calibrating the temperature input measurement.

23. The apparatus of claim 22, wherein calibrating the temperature input measurement comprises applying a correction factor between the actual temperature measurement and the temperature input measurement.

24. The apparatus of claim 1, wherein the memory comprises non-volatile memory.

25. The apparatus of claim 1, further comprising a first light source positioned to illuminate the biological sample.

26. The apparatus of claim 25, wherein the first light source is a laser or LED.

27. The apparatus of claim 25, wherein the one or more programs further includes instructions for:
   applying a first excitation light from the first light source to trigger the light signal from the biological sample.

28. The apparatus of claim 27, wherein the one or more programs further includes instructions for:
   not applying the first excitation light from the first light source to the biological sample at the first time.

29. The apparatus of claim 27, further comprising a second light source positioned to illuminate the biological sample, wherein the one or more programs further includes instructions for:
   applying a second excitation light from the second light source to trigger a light signal from the biological sample;
   detecting a third light input measurement from the first light sensor at a third time after triggering the light signal from the biological sample; and
   wherein the plurality of temperature input measurements further comprises a third temperature input measurement detected at the third time;
   using the first light input measurement to estimate noise signal; and
   using the plurality of temperature measurements to further estimate noise signal and improve noise suppression, thereby determining the light signal from the biological sample at the third time.

30. The apparatus of claim 29, wherein the first excitation light is a different wavelength than the second excitation light.

31. The apparatus of claim 30, wherein the one or more programs further includes instructions for:
   not applying the first excitation light from the first light source to the biological sample at the first time; and
   not applying the second excitation light from the second light source to the biological sample at the first time.

32. The apparatus of claim 31, wherein the one or more programs further includes instructions for:

not applying the first excitation light from the first light source to the biological sample at the third time; and
not applying the second excitation light from the second light source to the biological sample at the second time.

33. The apparatus of claim 1, wherein the light signal from the biological sample is triggered via a chemical reaction.

34. A method for amplification of a nucleic acid in a biological sample, the method comprising:
contacting the biocompatible coating of the apparatus of claim 1 with (i) the biological sample and (ii) reagents for amplification of nucleic acid in the sample, wherein said contacting forms a reaction mixture on the biocompatible coating of the apparatus;
using the apparatus to perform a nucleic acid amplification reaction; and
receiving results of the nucleic acid amplification reaction, the results including light emission data measured by the apparatus.

35. The method of claim 34, wherein at least two distinct reaction mixtures are formed on the biocompatible coating of the apparatus.

36. The method of claim 34, wherein said light emission data is selected from the group consisting of fluorescent light emission data and chemi-luminescent light emission data.

* * * * *